(12) United States Patent
Mesher

(10) Patent No.: US 9,860,962 B2
(45) Date of Patent: Jan. 2, 2018

(54) LIGHT EMISSION POWER CONTROL APPARATUS AND METHOD

(71) Applicant: TETRA TECH, INC., Pasadena, CA (US)

(72) Inventor: Darel Mesher, Spruce Grove (CA)

(73) Assignee: TETRA TECH, INC., Pasadena, CA (US)

( * ) Notice: Subject to any disclaimer, the term of this patent is extended or adjusted under 35 U.S.C. 154(b) by 0 days.

(21) Appl. No.: 15/291,335

(22) Filed: Oct. 12, 2016

(65) Prior Publication Data

US 2017/0034892 A1    Feb. 2, 2017

Related U.S. Application Data

(63) Continuation-in-part of application No. 14/724,925, filed on May 29, 2015, and a continuation-in-part of application No. 14/724,884, filed on May 29, 2015, and a continuation-in-part of application No. 14/724,890, filed on May 29, 2015.

(60) Provisional application No. 62/104,888, filed on Jan. 19, 2015, provisional application No. 62/104,882, filed on Jan. 19, 2015, provisional application No. 62/104,886, filed on Jan. 19, 2015.

(51) Int. Cl.
| | | |
|---|---|---|
| *B60Q 1/26* | (2006.01) |
| *H05B 37/02* | (2006.01) |
| *B61L 23/04* | (2006.01) |
| *G01B 11/30* | (2006.01) |
| *G01N 21/25* | (2006.01) |
| *B61K 9/08* | (2006.01) |

(52) U.S. Cl.
CPC ......... *H05B 37/0227* (2013.01); *B61K 9/08* (2013.01); *B61L 23/042* (2013.01); *B61L 23/048* (2013.01); *G01B 11/303* (2013.01); *G01N 21/251* (2013.01); *G01N 21/255* (2013.01); *G01N 2201/06113* (2013.01)

(58) Field of Classification Search
CPC ........... B61K 9/08; B61K 9/10; B61L 23/042; B61L 23/044–23/045; B61L 23/047
See application file for complete search history.

(56) References Cited

U.S. PATENT DOCUMENTS

| | | | | |
|---|---|---|---|---|
| 5,743,495 A * | 4/1998 | Welles, II | ............. | B61L 23/047 246/121 |
| 6,768,551 B2 | 7/2004 | Mian et al. | | |
| 8,190,377 B2 * | 5/2012 | Fu | ........................ | G01K 13/06 104/93 |
| 8,412,393 B2 * | 4/2013 | Anderson | ................ | B61K 9/08 246/121 |
| 8,724,904 B2 * | 5/2014 | Fujiki | .................. | G06K 9/6284 382/104 |
| 8,934,007 B2 * | 1/2015 | Snead | ....................... | G01L 1/24 348/125 |

(Continued)

OTHER PUBLICATIONS

Gingras, Denis, "Optics and Photonics Used in Road Transportation", INO, 369 rue Franquet, Sainte-Foy, Qc, Canada G1P 4N8 (Sep. 24, 1998).

*Primary Examiner* — Jason M Crawford
(74) *Attorney, Agent, or Firm* — Robinson IP Law, PLLC

(57) ABSTRACT

A system and method for adjusting light emitter output for a railway track inspection system based on data feedback from one or more sensors.

9 Claims, 9 Drawing Sheets

(56) References Cited

U.S. PATENT DOCUMENTS

| | | | |
|---|---|---|---|
| 2001/0045495 A1* | 11/2001 | Olson | B61L 23/044 246/121 |
| 2006/0017911 A1* | 1/2006 | Villar | B61K 9/08 356/4.01 |
| 2006/0098843 A1* | 5/2006 | Chew | B61K 9/08 382/103 |
| 2008/0303656 A1* | 12/2008 | Mathews, Jr. | B61L 1/20 340/540 |
| 2008/0304065 A1* | 12/2008 | Hesser | E01B 35/00 356/400 |
| 2009/0073428 A1* | 3/2009 | Magnus | B61K 9/08 356/237.1 |
| 2014/0151512 A1* | 6/2014 | Cooper | B61L 5/18 246/1 C |

* cited by examiner

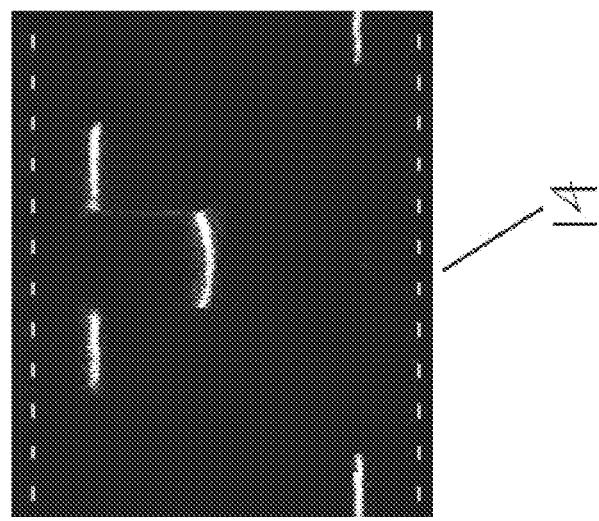
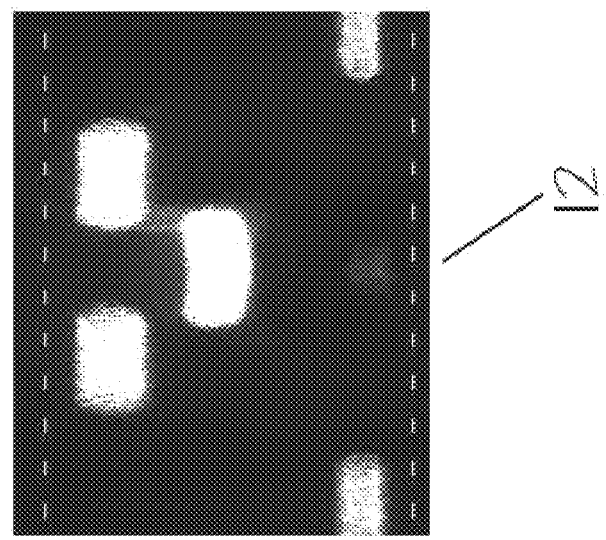
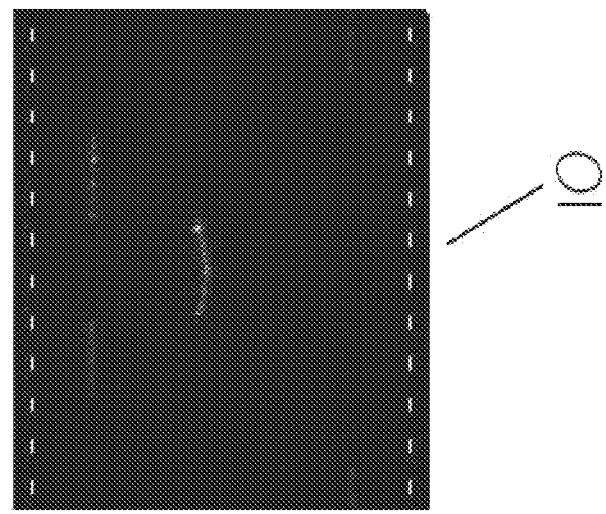
FIG. 2

LIGHT EMISSION POWER CONTROL APPARATUS AND METHOD

CROSS-REFERENCE(S) TO RELATED APPLICATION(S)

This application is a continuation-in-part application claiming priority to U.S. patent application Ser. No. 14/724,925 entitled "Light Emission Power Control Apparatus and Method" which was filed on May 29, 2015, which claims priority to U.S. Provisional Patent Application Ser. No. 62/104,888 entitled "Laser Power Control Apparatus and Method" which was filed on Jan. 19, 2015. This application is also a continuation-in-part application claiming priority to U.S. patent application Ser. No. 14/724,884 entitled "Protective Shroud" which was filed on May 29, 2015, which claims priority to U.S. Provisional Patent Application Ser. No. 62/104,882 entitled "Protective Shroud" which was filed on Jan. 19, 2015. This application is also a continuation-in-part application claiming priority to U.S. patent application Ser. No. 14/724,890 entitled "Sensor Synchronization Apparatus and Method" which was filed on May 29, 2015, which claims priority to U.S. Provisional Patent Application Ser. No. 62/104,886 entitled "Sensor Synchronization Apparatus and Method" which was filed on Jan. 19, 2015. All of the applications listed above are incorporated herein by reference in their respective entireties as if fully set forth herein.

FIELD

This disclosure relates to the field of railway track inspection and assessment systems.

BACKGROUND

Rail infrastructure owners are motivated to minimize staff exposure to unsafe environments and replace the time consuming and subjective process of manual crosstie (track) inspection with objective and automated processes. The motivation is driven by the desire to improve rail safety in a climate of increasing annual rail traffic volumes and increasing regulatory reporting requirements. Objective, repeatable, and accurate track inventory and condition assessment also provide owners with the innovative capability of implementing comprehensive asset management systems which include owner/region/environment specific track component deterioration models. Such rail specific asset management systems would yield significant economic benefits in the operation, maintenance and capital planning of rail networks. A primary goal of such automated systems is the non-destructive high-speed assessment of railway track infrastructure. Track inspection and assessment systems currently exist including, for example, Georgetown Rail (GREX) Aurora 3D surface profile system and Ensco Rail 2D video automated track inspection systems. Such systems typically use coherent light emitting technology, such as laser radiation, to illuminate regions of the railway track bed during assessment operations.

The effect of variations in surface properties of railroad tracks and surrounding surfaces has a significant impact on light levels reflected from these surfaces and subsequently detected by 3D sensors. Reflected light levels entering the sensors are not always optimum due to variations surface color (light or dark colored surfaces) or texture for example. Incorrect lighting levels can cause the 3D track surface profile measured by a 3D sensor to be distorted or imperceptible, affecting the measured profile accuracy.

In such systems, high power laser light sources may be used. Laser line projectors may include high power (Class IV) non-visible infrared laser sources (for example; a wide fan angle) (75-90° laser with a wavelength of 808 nm and a power of 10 watts). All Class IV lasers present an extreme ocular exposure hazard when used without external eye protection. Further complicated by the non-visible nature of infrared radiation (deactivating the natural aversion reflexes such as protective pupil contraction, blink, or head turn), Class IV lasers are capable of causing severe eye damage through direct, or reflected light exposure. Reflected exposure occurs when the laser radiation is scattered from highly reflective specular (shiny) targets such as polished metal surfaces (for example in the track environment; rail heads, switches, frogs). In environments where specular reflections are possible, any potential occurrence of exposure must be removed by eliminating ocular access to the beam. Beam access can be restricted by either requiring that protective eyewear (appropriately filtered) be worn by all those with any exposure potential, or by effectively enclosing the beam.

For rail testing environments with moving surveys using Class IV lasers, the top of the rail head presents a nearly ideal continuous omnidirectional specular reflector. In addition to the rail head, other flat or otherwise smooth surfaces (plates, switches, frogs, the materials between and around the rail head near crossings in urban areas), create conditions where the Maximum Permissible Exposure (MPE) limits for ocular damage are exceeded (especially in situations where those surfaces are wet). Adding to the danger of reflected laser energy, the non-divergent nature of laser sources guarantees that any reflected coherent laser light will present an ocular danger for large distances from the reflecting surfaces.

What is needed, therefore, is a way to control high powered light emitters used in systems similar to those described above in real time in order to limit unnecessary exposure to light emitted from such light emitters.

SUMMARY

A system for inspecting a railway track is disclosed wherein the system includes a power source (e.g., a gas powered engine providing electrical power, a generator or a battery); an adjustable intensity light emitting apparatus powered by the power source for emitting light energy toward a railway track; and a sensor for sensing the emitted light from the light emitting apparatus and acquiring three dimensional image data of the railway track to be stored in a data storage apparatus. The image data is preferably elevation (or range) and intensity data gathered using a 3D sensor. The system also includes at least one processor for controlling the optical power output of the light emitting apparatus, to adjust and compensate for changes in track bed color and texture variations and improve the ability to measure track bed profiles by 3D sensors. This ability to adjust the optical power output based on track surface characteristics provides improved accuracy railway track elevation and intensity measurements over a much wider range of real world conditions.

In one example the track bed surface is predominantly dark colored due, for example, to the placement of new wooden ties or localized grease contamination from lubricating devices, and the intensity of the light emitting source illuminating the track bed must be increased to reduce the number of undetectable reflected light areas in the profile measured by the 3D sensors. For typical 3D sensors, such dark areas which cause low intensity reflections can result in elevation zero value errors. Elevation zero value errors in 3D elevation and intensity profiles negatively impact the ability to generate accurate 3D elevation and intensity maps of the track bed surface thereby reducing the accuracy of subsequent inspection and assessment analysis.

In a related example the surface of the track bed is light colored due, for example, to the placement of concrete ties or localized light colored surface contaminations from fine soils due to mud holes, and the intensity of the light emitting source illuminating the track bed must be decreased to reduce the number of out-of-range reflected light areas in the profile measured by the 3D sensors. For typical 3D sensors, such high intensity reflections from light colored areas result in sensor saturation or out-of-range intensity conditions which produce invalid elevation measures. High intensity based out-of-range errors in 3D elevation and intensity profiles diminish the ability to generate accurate 3D elevation and intensity maps thereby reducing the accuracy of subsequent track bed inspection and assessments.

To compensate for undesirable light conditions, a system is disclosed for inspecting a railway track configured to adjust the intensity of a light emitting apparatus based on light reflected from a railway track, the system comprising a power source; a light emitting apparatus powered by the power source for emitting light energy toward a railway track; at least one sensor for sensing reflected light emitted from the light emitting apparatus; and a processor in communication with the at least one sensor wherein the processor includes an algorithm for adjusting the power of the light emitting apparatus, the algorithm comprising the steps of (a) calculating one or more intensity histograms based on the reflected light sensed by the at least one sensor; and (b) adjusting a light emitter control output value based at least in part on the calculated one or more intensity histograms; and a controller in communication with the processor wherein the controller is configured to control the light intensity of the light emitting apparatus in response to the light emitter control output value.

In certain embodiments, the algorithm for adjusting the power of the light emitting apparatus further comprises the step of calculating one or more aggregate intensity histograms for a target zone. In some example embodiments, the target zone further comprises at least one surface zone including one or more members selected from the group consisting of a gage tie zone, a rail zone, a field tie zone, and a field ballast zone. In some example embodiments, the algorithm for adjusting the power of the light emitting apparatus further comprises the steps of calculating a median histogram for the target zone and adjusting a light emitter control output value based at least in part on the calculated median histogram.

The algorithm for adjusting the power of the light emitting apparatus may further comprise the steps of calculating aggregate zero value error counts for the target zone and adjusting a light emitter control output value based at least in part on the calculated aggregate zero value error counts. Alternatively or additionally, the algorithm for adjusting the power of the light emitting apparatus further comprises the steps of calculating aggregate out-of-range error counts for the target zone and adjusting a light emitter control output value based at least in part on the calculated aggregate out-of-range error counts.

The algorithm for adjusting the power of the light emitting apparatus may further comprise the step of determining whether the number of zero value errors are greater than a zero value error count number threshold. Additionally or alternatively, the algorithm for adjusting the power of the light emitting apparatus further comprises the step of determining whether the number of out-of-range errors are greater than a range error count number threshold.

A system for inspecting a railway track is disclosed wherein the system is configured for disabling or otherwise cutting off power to a light emitting apparatus under certain conditions. The system is configured for inspecting a railway track configured to adjust the intensity of a light emitting apparatus based on the motion of the system relative to an adjacent railway track. The system is mounted to a railway track vehicle and comprises a power source; a light emitting apparatus powered by the power source for emitting light energy toward a railway track; at least one motion detector for detecting the motion of the system relative to an adjacent railway track; a processor in communication with the at least one motion detector wherein the processor includes an algorithm for adjusting the power of the light emitting apparatus, the algorithm comprising the steps of (a) determining whether the system is moving relative to an adjacent railway track based on incoming data from the at least one motion detector, and (b) adjusting a light emitter control output value based at least in part on incoming data from the at least one motion detector; and a controller in communication with the processor wherein the controller is configured to control the light intensity of the light emitting apparatus in response to the light emitter control output value.

In one embodiment, the algorithm for adjusting the power of the light emitting apparatus further comprises the step of adjusting the light emitter control output value to a value that causes the controller to shut off power to the light emitting apparatus if the system is moving below a minimum speed relative to an adjacent railway track. In another embodiment, the algorithm for adjusting the power of the light emitting apparatus further comprises the step of adjusting the light emitter control output value to a value that causes the controller to provide power to the light emitting apparatus if the system is moving at or above a minimum speed relative to an adjacent railway track.

A method of inspecting a railway track bed using a light source with real time adjustable light emission is also disclosed, the method comprising the steps of emitting light from a mobile inspection system comprising a light source wherein the emitted light is emitted toward an adjacent railway track bed; detecting motion of the mobile inspection system relative to the adjacent railway track bed; adjusting a light emitter control output value based on the detected motion of the mobile inspection system; and controlling the light intensity of the light emitting apparatus in response to the adjusted light emitter control output value. In embodiments, the detecting step further comprises detecting the speed of the system relative to the adjacent railway track bed. The adjusting step may further include adjusting the control output value to a value that causes the power to the light emitting apparatus to be shut off if the detected speed of the railway track vehicle falls below a minimum speed threshold. Additionally or alternatively, the adjusting step may include adjusting the control output value to a value that causes the power to the light emitting apparatus to be activated if the detected speed of the railway track vehicle is equal to or greater than a minimum speed threshold.

The controlling step may further include disabling power to the light emitting apparatus in response to the control output value and/or activating power to the light emitting apparatus in response to the control output value.

The summary provided herein is intended to provide examples of particular disclosed embodiments and is not intended to limit the scope of the invention disclosure in any way.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

FIG. 2 shows 3D sensor intensity profile for reflected light levels for dark, light, and normal surfaces, respectively for the profile of the same arbitrary stepped elevation object;

The figures are provided to illustrate concepts of the invention disclosure and are not intended to limit the scope of the invention disclosure to the exact embodiments provided in the figures.

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

"Track", "Railway track", "track bed" or "railway track bed" is defined herein to mean a section of railway including the rails, ties, components holding the rails to the ties, and ballast material.

"Sample" or "profile" is defined herein to include a discrete measurement of reflected light during a specifically defined time period.

A "processor" is defined herein to include a processing unit including, for example, one or more microprocessors, an application-specific instruction-set processor, a network processor, a vector processor, a scalar processor, or any combination thereof, or any other control logic apparatus now known or later developed that is capable of performing the tasks described herein, or any combination thereof.

The phrase "in communication with" means that two or more devices are in communication with one another physically (e.g., by wire) or indirectly (e.g., by wireless communication).

"Motion Detector" is broadly defined as anything from a simple motion detector to a device configured to detect the speed of a vehicle such as, for example, a speedometer or a shaft encoder.

Figure 1:
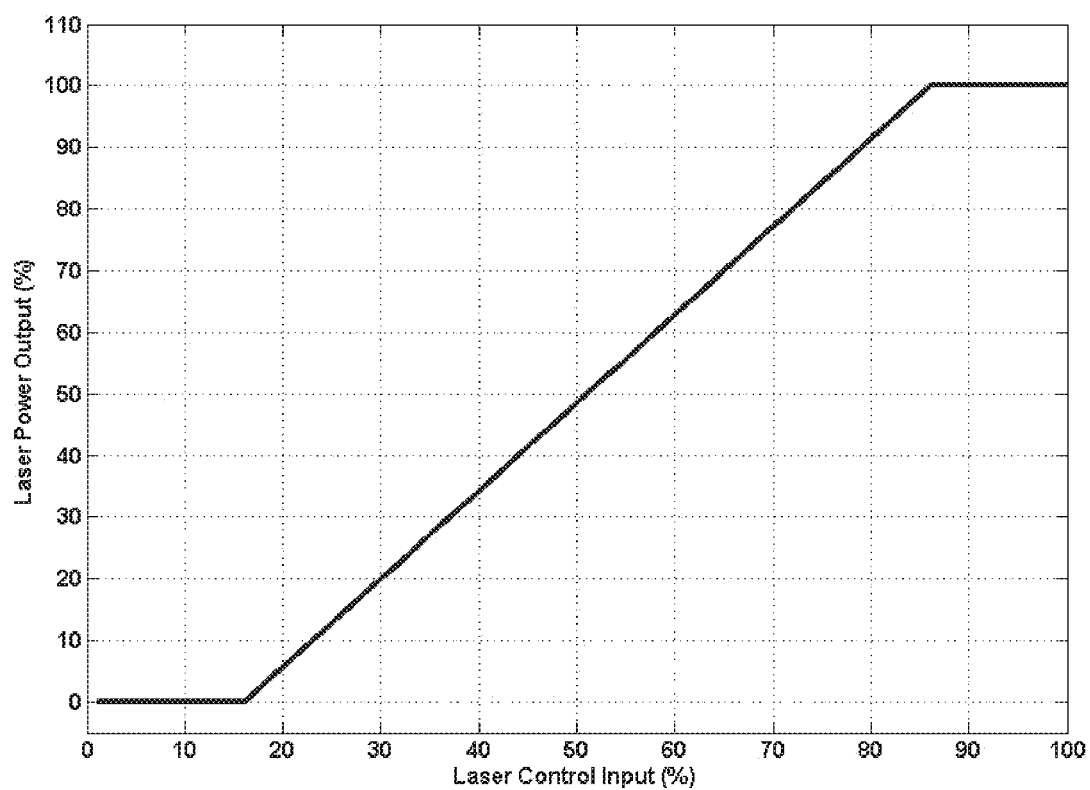
FIG. 1 shows a graphical relationship between the control port input versus output power for a typical light emission source.

Wide fan-angle line generators used in track inspection and assessment systems are typically high power Class IV, non-visible infrared laser sources (nominally wavelength of 808 nm with a maximum power output of 10 watts in this example embodiment). These laser devices typically have a power control input port, allowing the direct control of the emitted laser optical output power. Based on the control signals applied to the control port, the radiated laser power can be adjusted from 0 to 100 percent of the rated maximum output power. Adjustments to this control port are substantially instantaneous. A graphical representation of a typical laser control port input versus laser output power is shown in FIG. 1.

In a preferred embodiment, the uniform intensity line generated by a wide fan-angle light source is projected onto a surface of a track bed and is reflected and sensed by one or more sensors. The intensity detected by the sensors is a complex function of the characteristics of the surface illuminated by the light source. Of particular importance are the surface properties of texture, uniformity, and color. Changes in surface physical properties result in changes in reflected light levels. Light levels deviating substantially from mid-range negatively impact 3D elevation measurements. Low light levels result in missing or zero values for sections of a measured 3D elevation profile, and excessively high light levels can cause sensor saturation and introduce intensity out-of-range errors that result in measured elevation range errors.

It is not uncommon to have wide variations in the physical surface characteristics affecting reflected light levels during track surveys. These variations can be compensated for by adjusting the radiated light optical power (intensity) based on the track surface conditions on a near real-time basis during survey data collection. To this end, disclosed herein is a method of measuring surface elevation of a track bed using at least one 3D sensor, analyzing measured elevation and intensity data (for elevation zero value errors, out-of-range errors, and intensity distribution) and adjusting light emitter control voltage based on such analysis to improve measured 3D elevation data quality.

Figure 3:
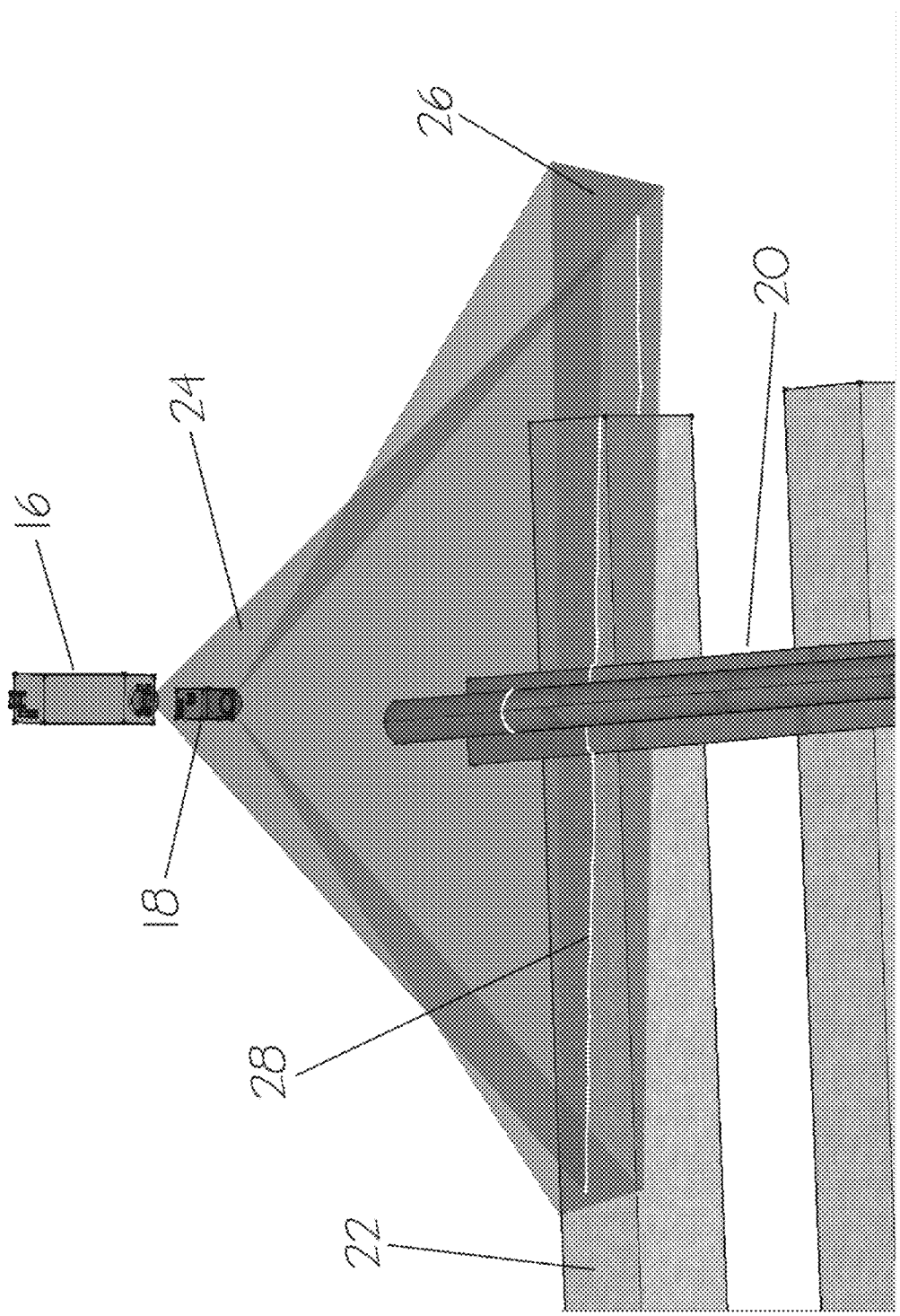
FIG. 3 shows a somewhat schematic diagram of a fixed output light line projector being used to illuminate a normal colored object and the resulting typical reflected normal line intensity detected by a 3D sensor.
Figure 4:
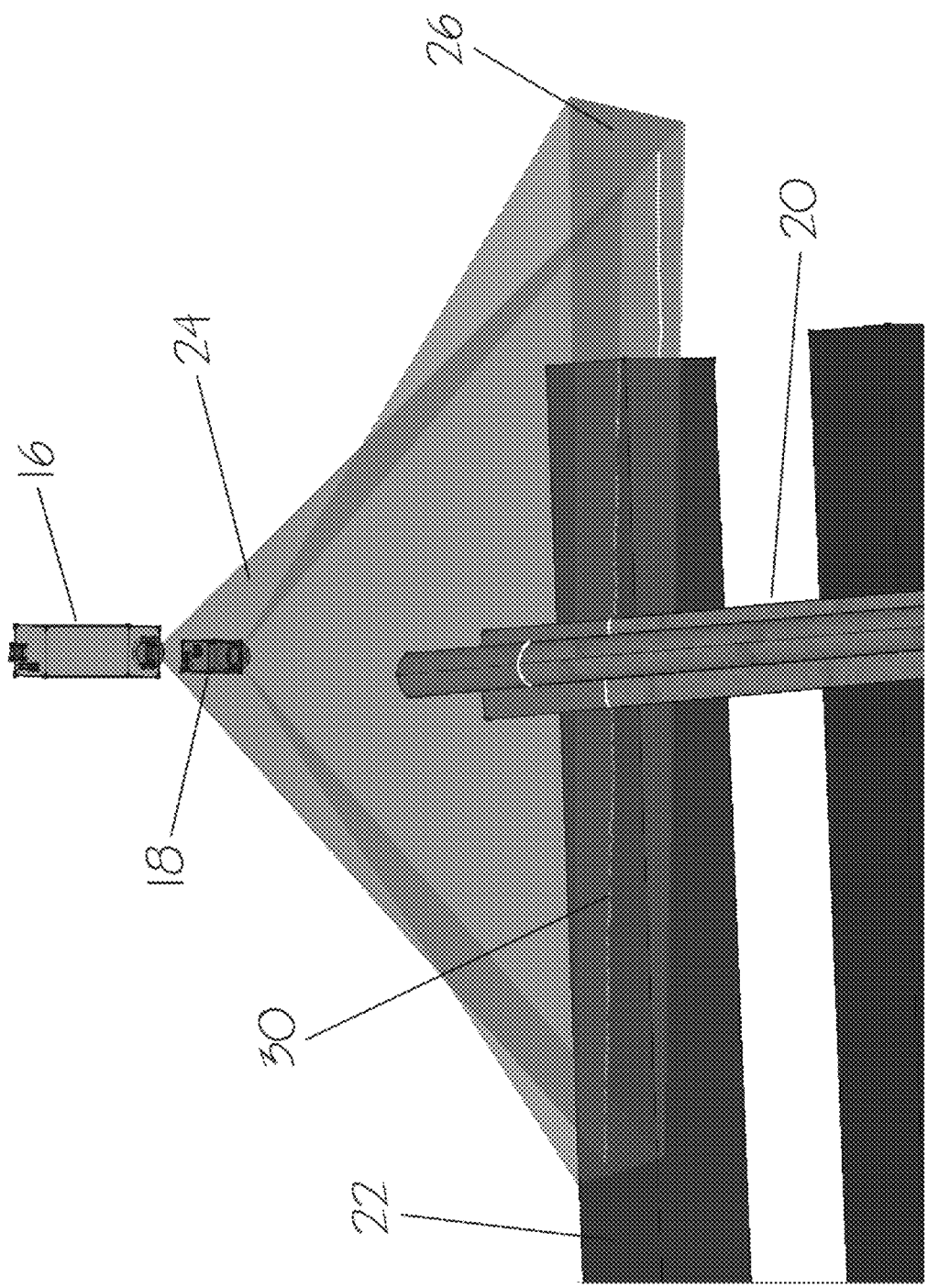
FIG. 4 shows a somewhat schematic diagram of a fixed output light line projector being used to illuminate a dark colored object and the resulting typical reflected low line intensity detected by a 3D sensor.
Figure 5:
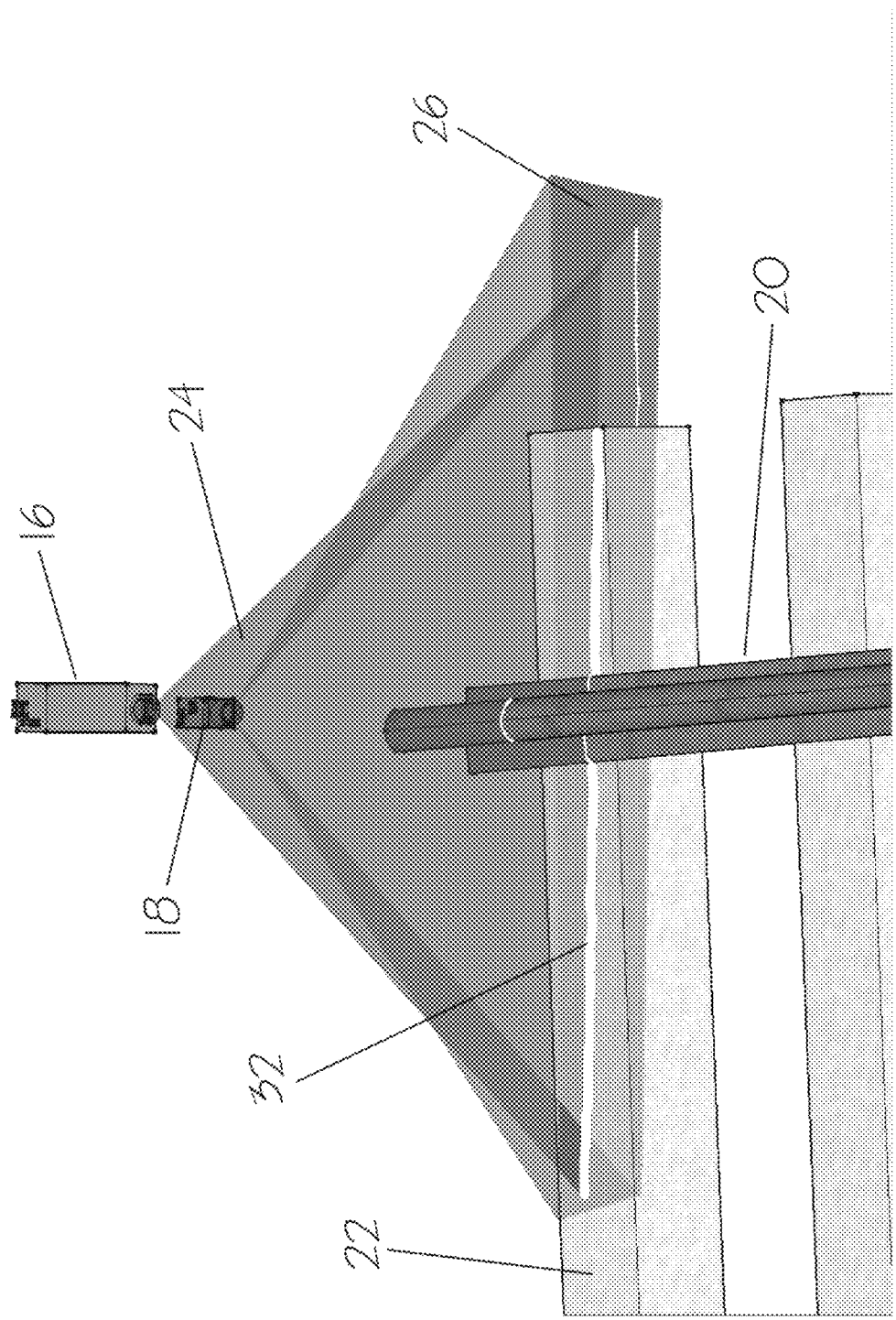
FIG. 5 shows a somewhat schematic diagram of a fixed output light line projector being used to illuminate a light colored object and the resulting typical reflected high line intensity detected by a 3D sensor

The effect of variations in surface properties (surface color in this example) on light 3D profile line intensity is demonstrated in FIGS. 2 through 5. Dark color surfaces reflect less energy (representing undetectable elevations within the measured profiles which are reported as elevation "Zero Value Errors") as shown in the dark color surface image 10 in FIG. 2, and light color surfaces reflect more light for a given source radiated power (intensity) as shown in the light color surface image 12 in FIG. 2. A normal or average color surface is shown as the normal color surface image 14 in FIG. 2. The effect of surface color on reflected light levels is demonstrated for various crosstie colors in FIGS. 3 through 5. These figures include a light source 16 (e.g., a laser), a 3D sensor 18, a rail 20 and a tie 22. The light source 16 casts a light beam having a wide fan-angle 24. The 3D sensor 18 has a wide field of view 26 as shown in FIG. 3, and a 3D profile 28 can be seen where the light strikes the surface of the tie 22 and rail 20. FIG. 3 shows moderate or normal light conditions resulting in a normal and desirable 3D profile line 28 intensity. FIG. 4 shows an example in which a low 3D profile 30 line intensity is acquired because of the presence of dark colored objects. Finally, FIG. 5 shows a resultant high 3D profile line 32 intensity when light colored objects are encountered.

Figure 6:
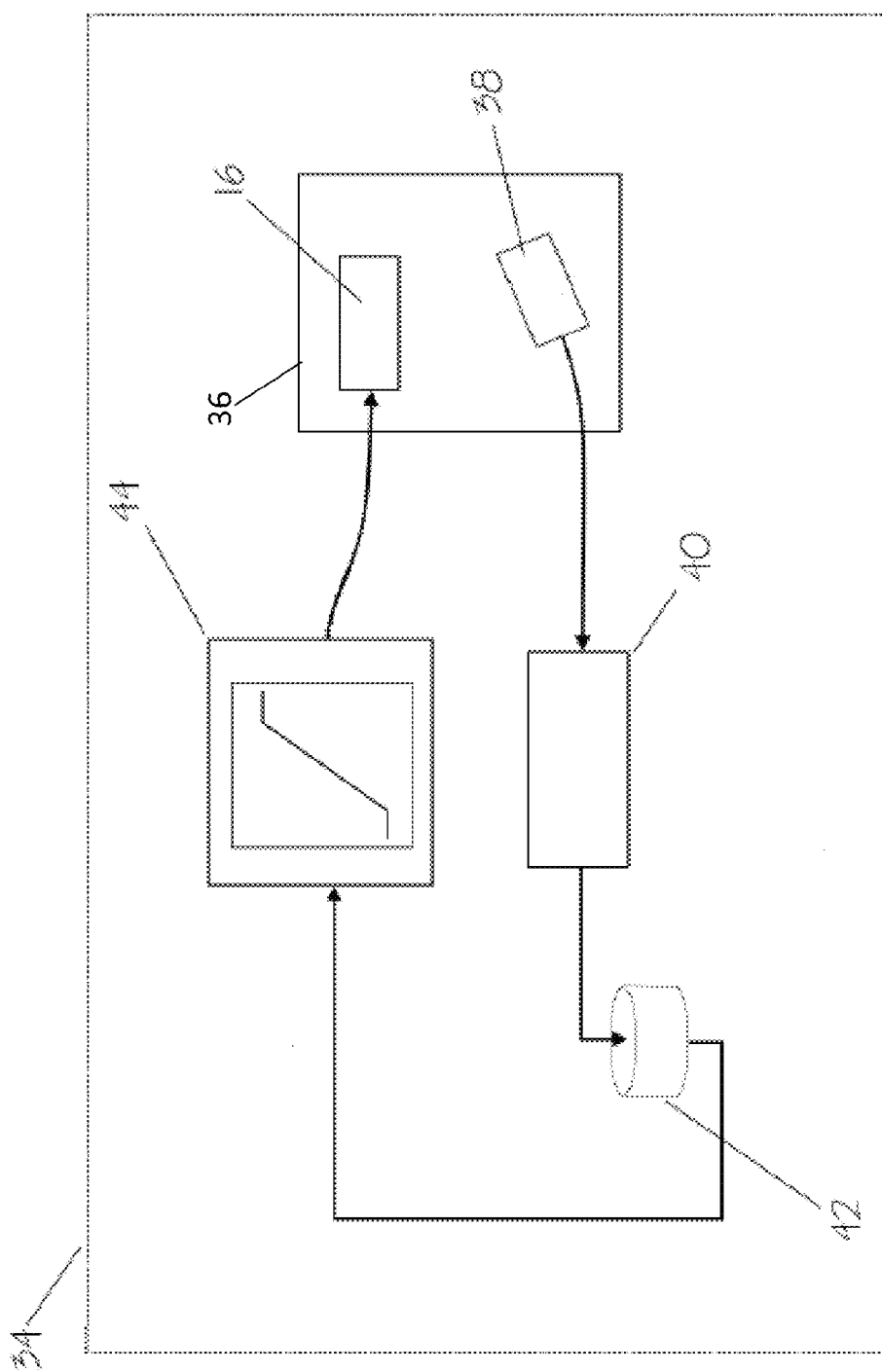
FIG. 6 shows a block diagram of a light emission source power control system.

FIG. 6 shows a light emitter power control system 34 including an enclosure 36 that includes a light source 16 and a 3D sensor 38. A processor 40 is shown for processing data collected from the 3D sensor wherein such data is stored in one or more sensor data storage devices 42. A light power controller 44 in communication with the processor 40 controls the output optical power of the emitted light based on the analysis of data compiled by the 3D sensor 38. The light emitter power control system 34 preferably includes a collection of independent processes operating concurrently during active survey data collection. Processes are defined to interface, control and stream the surface elevation and surface reflection intensity data for each applicable 3D sensor. These data streams are segmented into fixed length and width 3D elevation and intensity maps as separate data files, where each data file is preferably defined for example as 1.6 m wide and 30.5 m long segments of track for each applicable 3D sensor.

Figure 7:
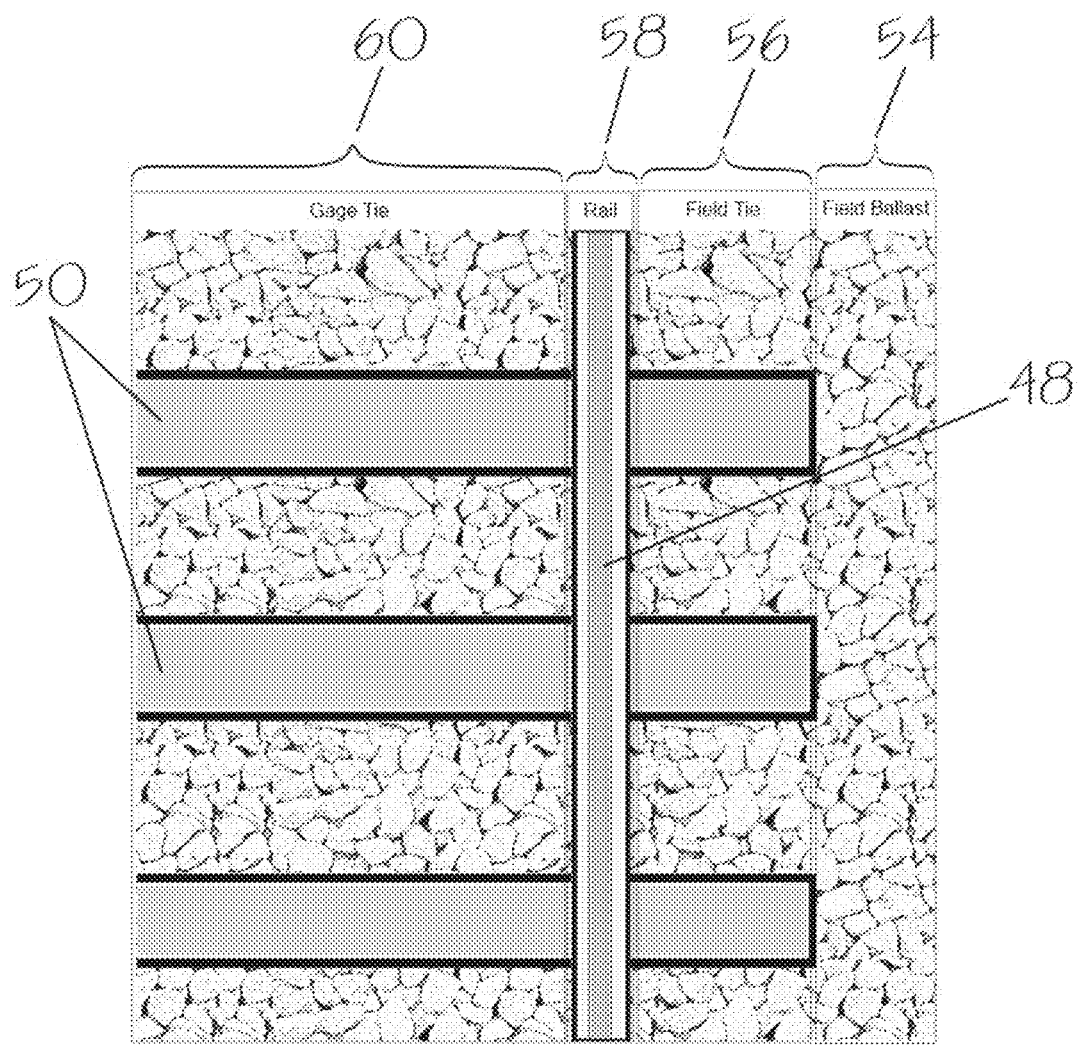
FIG. 7 shows track bed transverse zones defined and used by a light emission power control process to characterize profile intensity data based on the location where the data was gathered.

A primary light emitter power control process running on the processor 40 monitors the 3D sensor elevation and intensity data streams in real time and preferably calculates aggregate 3D surface intensity histograms, an elevation Zero Value Error count, and an Out-of-Range Error count. The mathematical combination or aggregation of individual scan line intensity values, longitudinally in the direction of survey, is an efficient method to produce representative intensity measures required for real-time laser power control. To maximize efficiency and processing speed, intensity values from the same lateral offset, representing the same scan column, are processed in aggregate. The number longitudinal scan line samples aggregated together should be preferably selected to be large enough to minimize the influence of data outliers (more than 1000 values for example) and small enough to be processed in real-time (1000 or less for example). Following fixed column based processing of scan intensity measures over a longitudinal interval, a single aggregate measure is produced for each column. This method of producing aggregate measures for each scan column is applied continuously in the survey direction during data collection. The aggregated intensity measures are further processed to produce histograms for each zone (as shown in FIG. 7, a ballast zone 54, a field tie end zone 56, a rail zone 58, and a gage zone 60) across the track bed. These zones defined by transverse offsets across the track bed are based substantially on sensor location and crosstie dimensions. If, in one example, the zones defined in FIG. 7 have widths of 600 columns for gage tie zone 60, 150 columns for rail zone 58, 470 columns for field tie end zone 56, and 316 columns for ballast zone 54, then the total scan width would be 1536 columns. If in this example, 1000 longitudinal scans are used to calculate the aggregate intensity measures for each zone, then the gage tie zone 60 would result in an input matrix of intensity values that is 1000 rows by 600 columns producing a single aggregate measurement vector of length 600. Similar calculations for the remaining zones would produce aggregated intensity vectors of length 150 for zone 58, length 470 for zone 56, and length 316 for zone 54. A histogram for each of these aggregate zone intensity vectors is then calculated and the histograms are then used for track bed light emitter power control analysis. The process is repeated continuously and in substantially real-time during surveys.

FIG. 7 shows a segment of one half of the track bed surface with a width that is defined by the field of view of a single sensor centered over the rail. The track bed section shown in FIG. 7 contains a rail 48, a plurality of cross ties 50, and four separate transverse light emitter power control analysis zones as described above. These analysis zones correspond to the following: the ballast zone 54, the transverse section of track bed on the field side of the rail containing ballast only; the field tie end zone 56, the transverse section of track bed on the field side of the rail containing crosstie ends; the rail zone 58, the transverse section of track bed containing the rail; and the gage zone 60, the transverse section of track bed on the gage side of the rail containing crossties as shown in FIG. 7. The mean, median, maximum, minimum and other light intensity statistics, for example, are preferably calculated continuously for defined longitudinal intervals (for example, for each 5 meters along the track bed) for each aggregate parameter in each transverse zone. A new sample or profile of light intensity data preferably occurs about every 2 mm to about every 6 mm in the longitudinal direction depending on the speed of the 3D sensor 38.

Figure 8:
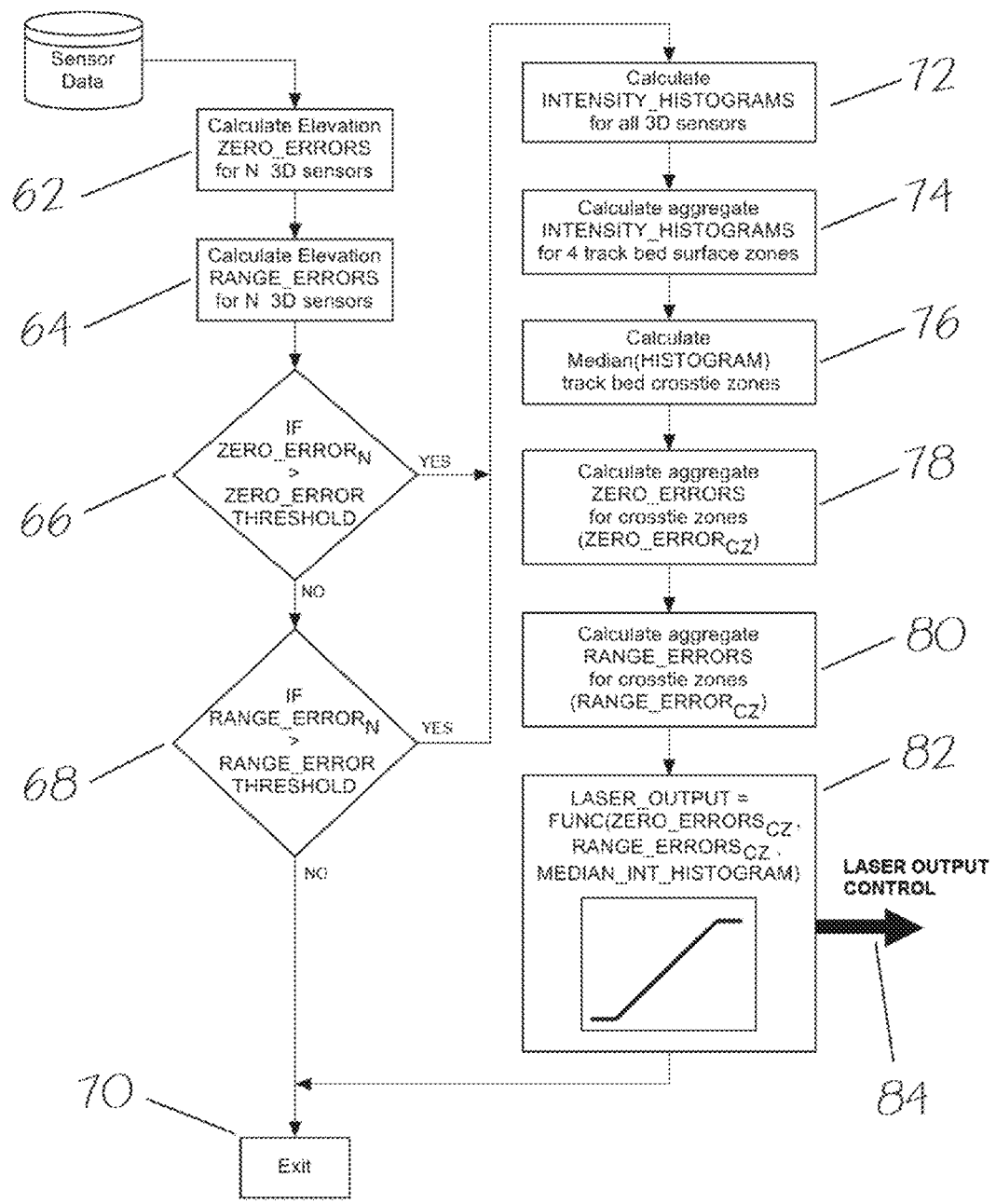
FIG. 8 shows a flow chart illustrating a light emission power control algorithm used by a light emission power control process.

A light emitter power control output value is adjusted if error conditions are detected (based on the Elevation Zero Value Error count and Range Error count) which exceed acceptable maximum error count thresholds. If a significant number of sensor elevation errors or out-of-range intensity errors are detected, the laser control power output level is adjusted based on the track bed surface intensity values for zones containing ties. The updated light emission power control value is increased if the profile intensity median value is less than a target intensity value, and decreased if the intensity median value is greater than the target intensity value. These steps are depicted as an algorithm in the flow chart shown in FIG. 8.

3D sensor data is gathered in real time and zero value errors are calculated for each of the sensors (block 62). Out-of-Range errors are then calculated as shown in block 64. Then, a determination is made as to whether any of the sensor zero value error counts are greater than a predefined zero value error count threshold (block 66). If the maximum number of zero value errors for all sensors is below the zero value error count threshold, and the maximum number of out-of-range errors for all sensors is less than the range error count threshold (block 68) then the system exits without change to the light emitter control output signal as shown in block 70. If, however, any sensor zero value error count exceeds the zero value error count threshold or if any of the sensor out-of-range error counts exceed the range error count threshold, the light emitter power control output signal is adjusted to reduce sensor errors caused by higher than optimum radiated light source optical power. In order to calculate the correct laser control signal adjustment, intensity histograms are calculated for each of the applicable sensors (block 72), and then aggregate intensity histograms are preferably calculated for each of the light emitter power control analysis zones including the field ballast zone, the field tie zone, the rail zone, and the gage tie zone (block 74). Median histograms are then calculated (block 76). Aggregate zero value error counts are then calculated for each analysis zone (block 78), followed by aggregate out-of-range error counts (block 80). Then, light emitter power is adjusted based at least in part on the calculated zero error counts, range error counts and intensity histograms (block 82), resulting in an update of the Light emitter Output Control signal 84.

By providing a way to control laser optical output power based on measurement sensor feedback during railway track inspections, higher quality and more consistent 3D image data are achievable. With higher quality 3D imagery, a more accurate picture of overall railway structure is possible.

Another important issue to consider with the use of high power light emitting devices is safety and eye protection for persons in relative close proximity to light emitting devices. The various embodiments of the system described herein are preferably mounted on a railway track vehicle configured to move and be propelled along a railway track. Railway track vehicles of various kinds including trucks configured for travel along railroads are well known in the art and are not discussed in detail here.

Figure 9:
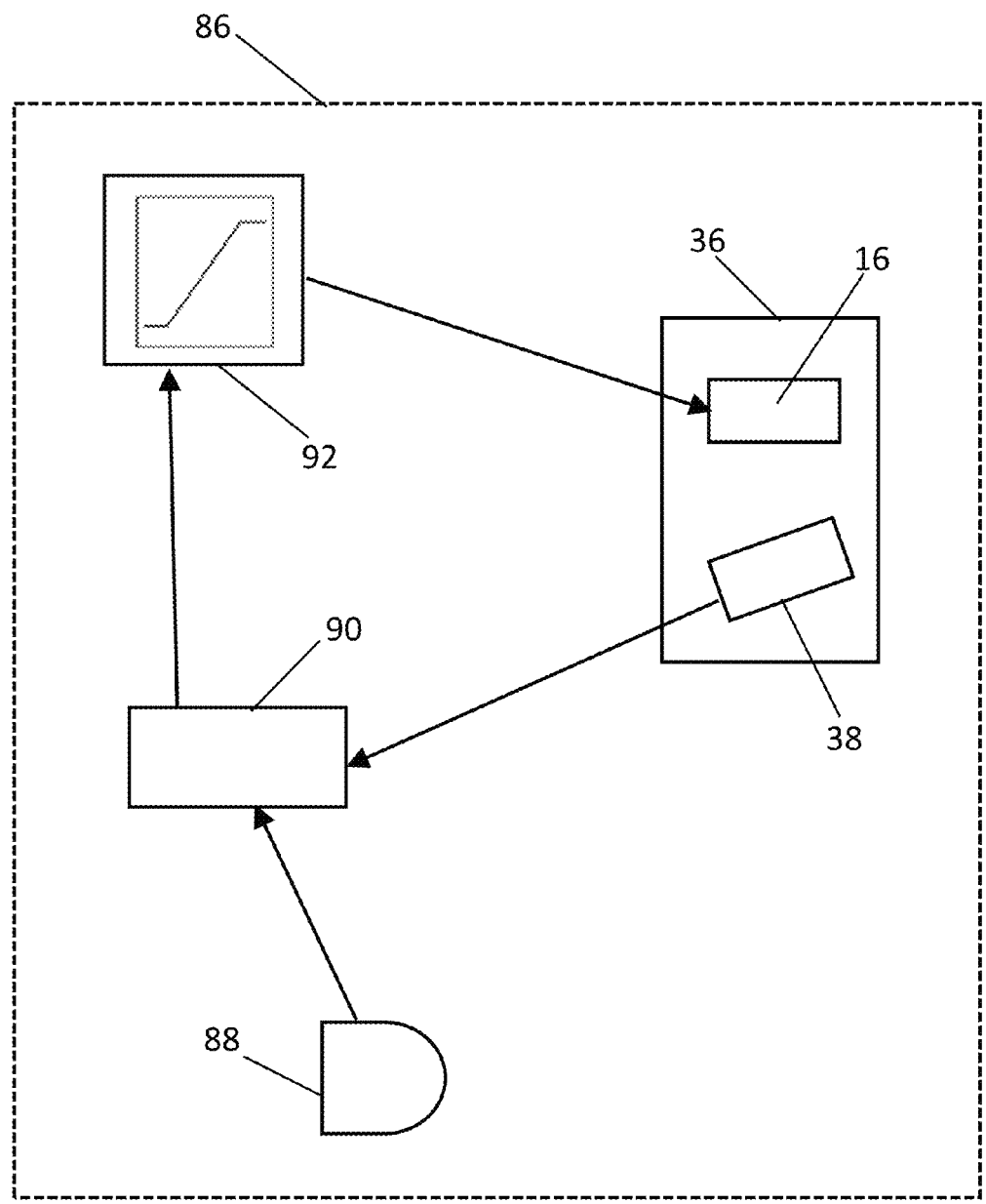
FIG. 9 shows a schematic diagram of a light emission source power control system configured to activate or deactivate a light emission apparatus under certain conditions.

In one embodiment, a system 86 for inspecting a railway track is mounted to a railway track vehicle. The system 86 is configured to adjust the intensity of a light emitting apparatus based on the motion of the system 86 relative to an adjacent railway track. The system 86, shown schematically in FIG. 9, includes a light emitting apparatus 16 for emitting light energy toward a railway track. The system 86 further includes at least one motion detector 88 for detecting the speed of the railway track vehicle on which the system 86 is mounted. The system further includes a processor 90 in communication with the at least one motion detector 88. The processor 90 includes an algorithm for adjusting the power of the light emitting apparatus 16 wherein the algorithm includes the steps of determining whether the system 86 is moving at a minimum speed relative to an adjacent railway track based on incoming data from the at least one motion detector 88, and adjusting a light emitter control output value based at least in part on incoming data from the at least one motion detector 88. The system further includes a controller 92 in communication with the processor 90 wherein the controller 92 is configured to control the light intensity of the light emitting apparatus 16 in response to the light emitter control output value.

When the system is moving below a minimum threshold speed, the processor 90 sends a control output value to the controller 92 that causes the controller to disable the light emitting apparatus 16 so that no light is emitted. The minimum threshold speed can be set at zero units of distance per time or another setting such as, for example, 2 miles per hour. When the system 86 is not moving along a track, the light emitting apparatus 16 is not being used to help gather data. Since there is a health risk with exposure to light emitted from the light emitting apparatus 16, the system 86 shuts off the light emitting apparatus 16 while it is not needed to help gather data. When the system 86 begins moving again above the minimum threshold speed, the light emitter control output value changes to a value that causes the controller 92 to activate or reactivate the light emitting apparatus 16. In one embodiment, the motion detector 88 only detects relative motion and does not detect speed. If the system 86 is in motion relative to an adjacent railway track, the light emitter control output value is set to a setting that causes the controller 92 to activate the light emitting apparatus 16. If the system 86 is not in motion relative to an adjacent railway track, the light emitter control output value is set to a setting that causes the controller 92 to deactivate the light emitting apparatus 16.

In a preferred embodiment, the motion detector 88 is a shaft encoder that produces pulses at a rate that corresponds to the speed at which a shaft rotates. The shaft encoder is configured to operate in conjunction with a shaft of the railway track vehicle on which the system 86 is mounted. So, when the railway track vehicle is not moving, the shaft encoder produces zero pulses. When the railway track vehicle is moving, the shaft encoder provides information to the processor 90 including the speed of the system 86 relative to an adjacent railway track.

The system 86 described above provides a number of important advantages including providing a system for automatically activating and deactivating a high-powered light emitting device based on motion of the system relative to an adjacent railway track. The system 86 allows for a minimum speed to be set so that a light emitting device is deactivated when the system speed falls below the minimum speed, thereby eliminating the eye exposure hazards associated with such high powered light emitting devices during times when the system or associated components are not actively scanning the adjacent railway track. When the system resumes motion and scanning, the system reactivates the light emitting device.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A system for inspecting a railway track configured to adjust the intensity of a light emitting apparatus based on the motion of the system relative to an adjacent railway track wherein the system is mounted to a railway track vehicle, the system comprising:
   a power source;
   a light emitting apparatus powered by the power source for emitting light energy toward a railway track;
   at least one motion detector for detecting the motion of the system relative to an adjacent railway track; and
   a processor in communication with the at least one motion detector wherein the processor includes an algorithm for adjusting the power of the light emitting apparatus, the algorithm comprising the steps of:
   a. determining whether the system is moving relative to an adjacent railway track based on incoming data from the at least one motion detector;
   b. adjusting a light emitter control output value based at least in part on incoming data from the at least one motion detector; and
   a controller in communication with the processor wherein the controller is configured to control the light intensity of the light emitting apparatus in response to the light emitter control output value.

2. The system of claim 1 wherein the algorithm for adjusting the power of the light emitting apparatus further comprises the step of adjusting the light emitter control output value to a value that causes the controller to shut off power to the light emitting apparatus if the system is moving below a minimum speed relative to an adjacent railway track.

3. The system of claim 1 wherein the algorithm for adjusting the power of the light emitting apparatus further comprises the step of adjusting the light emitter control output value to a value that causes the controller to provide power to the light emitting apparatus if the system is moving at or above a minimum speed relative to an adjacent railway track.

4. A method of inspecting a railway track bed using a light source with real time adjustable light emission, the method comprising the steps of:
   a. emitting light from a mobile inspection system comprising a light source wherein the emitted light is emitted toward an adjacent railway track bed;
   b. detecting motion of the mobile inspection system relative to the adjacent railway track bed;
   c. adjusting a light emitter control output value based on the detected motion of the mobile inspection system; and
   d. controlling the light intensity of the light emitting apparatus in response to the adjusted light emitter control output value.

5. The method of claim 4 wherein the detecting step further comprises detecting the speed of the system relative to the adjacent railway track bed.

6. The method of claim 5 wherein the adjusting step further comprises adjusting the control output value to a value that causes the power to the light emitting apparatus to be shut off if the detected speed of the railway track vehicle falls below a minimum speed threshold.

7. The method of claim 5 wherein the controlling step further comprises disabling power to the light emitting apparatus in response to the control output value.

8. The method of claim 4 wherein the adjusting step further comprises adjusting the control output value to a value that causes the power to the light emitting apparatus to be activated if the detected speed of the railway track vehicle is equal to or greater than a minimum speed threshold.

9. The method of claim 8 wherein the controlling step further comprises activating power to the light emitting apparatus in response to the control output value.

* * * * *